US012672961B2

(12) United States Patent
Stiehm et al.

(10) Patent No.: US 12,672,961 B2
(45) Date of Patent: Jul. 7, 2026

(54) VENOUS VALVE PROSTHESIS

(71) Applicant: CORTRONIK GmbH, Rostock (DE)

(72) Inventors: Michael Stiehm, Rostock (DE); Wolfram Schmidt, Rostock (DE); Niels Grabow, Rostock (DE); Jonas Keiler, Rostock (DE); Maria Reumann, Rostock (DE); Andreas Wree, Elmenhorst (DE); Andreas Hof, Luebeck (DE); Heinz Mueller, Rostock (DE); Carsten Momma, Rostock (DE); Klaus-Peter Schmitz, Rostock (DE); Karsten Koop, Rostock (DE); Julia Schubert, Rostock (DE); Kerstin Lebahn, Rostock (DE); Sabine Illner, Rostock (DE); Sabine Kischkel, Rostock (DE); Jonathan Ortelt, Rostock (DE)

(73) Assignee: BIOTRONIK AG, Buelach (CH)

( * ) Notice: Subject to any disclaimer, the term of this patent is extended or adjusted under 35 U.S.C. 154(b) by 867 days.

(21) Appl. No.: 17/918,810

(22) PCT Filed: Apr. 9, 2021

(86) PCT No.: PCT/EP2021/059287

§ 371 (c)(1),
(2) Date: Oct. 13, 2022

(87) PCT Pub. No.: WO2021/209334

PCT Pub. Date: Oct. 21, 2021

(65) Prior Publication Data

US 2023/0372103 A1 Nov. 23, 2023

(30) Foreign Application Priority Data

Apr. 17, 2020 (DE) .......................... 102020110490.1
Apr. 27, 2020 (DE) .......................... 102020111388.9

(51) Int. Cl.
*A61F 2/24* (2006.01)

(52) U.S. Cl.
CPC .... *A61F 2/2475* (2013.01); *A61F 2230/0017* (2013.01)

(58) Field of Classification Search
CPC ..... A61F 2/2475; A61F 2/2476; A61F 2/2418
See application file for complete search history.

(56) References Cited

U.S. PATENT DOCUMENTS 6,425,916 B1 * 7/2002 Garrison ............... A61F 2/2436
623/2.11
6,478,819 B2 * 11/2002 Moe ...................... A61F 2/2418
623/2.18

(Continued)

FOREIGN PATENT DOCUMENTS

EP        2628464 A1 * 8/2013 ........... A61F 2/2415
WO 2018102826 A1    6/2018

OTHER PUBLICATIONS

International Search Report from the corresponding International Patent Application No. PCT/EP2020/083711, dated Feb. 17, 2021.

*Primary Examiner* — Alvin J Stewart
(74) *Attorney, Agent, or Firm* — Greer, Burns & Crain, Ltd.; Steven P. Fallon

(57) ABSTRACT

A venous valve prosthesis for transporting a flow of body fluid in a vessel in a predetermined direction includes includes a hollow-cylindrical support structure. A skirt is connected to the support structure and forms a closed, circumferential jacket of the support structure. The prosthesis also includes a valve leaflet arrangement with a first valve leaflet and a second valve leaflet, each being connected to the skirt. A downstream edge of the first valve leaflet and a downstream edge of the second valve leaflet are opposite to each other and configured in such a manner that in a first state of the valve leaflet arrangement they form an opening (Continued)

for blood to flow through in the predetermined direction and in a second state of the valve leaflet arrangement the opening is closed and to prevent a backflow of blood in a direction opposite to the predetermined direction. A ratio of the inner diameter of the support structure to its length in the predetermined direction is at most 1.

19 Claims, 10 Drawing Sheets

(56)                    References Cited

U.S. PATENT DOCUMENTS

| | | | | |
|---|---|---|---|---|
| 7,198,646 | B2 * | 4/2007 | Figulla | A61F 2/2418 623/1.15 |
| 7,811,316 | B2 * | 10/2010 | Kalmann | A61F 2/2418 623/1.42 |
| 9,339,377 | B2 * | 5/2016 | Quadri | A61F 2/2412 |
| 11,589,981 | B2 * | 2/2023 | Girard | A61F 2/2412 |
| 12,029,646 | B2 * | 7/2024 | Hariton | A61F 2/24 |
| 12,232,957 | B2 * | 2/2025 | Straubinger | A61F 2/2418 |
| 12,318,281 | B2 * | 6/2025 | Girard | A61F 2/2469 |
| 12,472,058 | B2 * | 11/2025 | Levi | A61F 2/2418 |
| 2001/0021872 | A1 * | 9/2001 | Bailey | A61F 2/07 623/1.26 |
| 2001/0049556 | A1 * | 12/2001 | Moe | A61F 2/2418 623/2.14 |
| 2002/0151970 | A1 * | 10/2002 | Garrison | A61F 2/2433 623/2.14 |
| 2004/0236411 | A1 * | 11/2004 | Sarac | A61L 27/3641 623/2.14 |
| 2004/0260389 | A1 * | 12/2004 | Case | A61F 2/2475 623/2.38 |
| 2005/0075731 | A1 * | 4/2005 | Artof | A61F 2/2439 623/2.18 |
| 2005/0096735 | A1 * | 5/2005 | Hojeibane | A61F 2/2418 623/2.18 |
| 2005/0137676 | A1 * | 6/2005 | Richardson | A61F 2/2418 623/2.18 |
| 2005/0137681 | A1 * | 6/2005 | Shoemaker | A61F 2/06 623/1.23 |
| 2005/0137682 | A1 * | 6/2005 | Justino | A61F 2/2418 623/2.14 |
| 2006/0122686 | A1 * | 6/2006 | Gilad | A61F 2/2418 623/1.13 |
| 2006/0122692 | A1 * | 6/2006 | Gilad | A61F 2/2418 623/1.35 |
| 2006/0149360 | A1 * | 7/2006 | Schwammenthal | A61F 2/2418 623/1.36 |
| 2006/0190074 | A1 * | 8/2006 | Hill | A61F 2/2475 623/2.18 |
| 2006/0210597 | A1 * | 9/2006 | Hiles | A61L 31/047 623/2.14 |
| 2006/0282157 | A1 * | 12/2006 | Hill | A61F 2/2475 623/1.11 |
| 2007/0027535 | A1 * | 2/2007 | Purdy | A61F 2/2418 623/2.18 |
| 2007/0067021 | A1 * | 3/2007 | Haverkost | A61F 2/2412 623/2.18 |
| 2007/0100435 | A1 * | 5/2007 | Case | A61F 2/2418 623/901 |
| 2007/0239265 | A1 * | 10/2007 | Birdsall | A61L 27/303 623/2.11 |
| 2007/0288086 | A1 * | 12/2007 | Kalmann | A61F 2/2418 623/1.1 |
| 2007/0288087 | A1 * | 12/2007 | Fearnot | A61F 2/2418 623/2.18 |
| 2008/0046071 | A1 * | 2/2008 | Pavcnik | A61L 27/507 623/1.24 |
| 2008/0071369 | A1 * | 3/2008 | Tuval | A61F 2/2436 623/2.38 |
| 2008/0077236 | A1 * | 3/2008 | Letac | A61F 2/2433 623/2.18 |
| 2010/0036484 | A1 * | 2/2010 | Hariton | A61F 2/2418 623/2.18 |
| 2010/0204781 | A1 * | 8/2010 | Alkhatib | A61F 2/2418 623/1.26 |
| 2010/0262231 | A1 * | 10/2010 | Tuval | A61F 2/2409 623/2.4 |
| 2011/0098802 | A1 * | 4/2011 | Braido | A61F 2/243 623/2.11 |
| 2012/0053682 | A1 * | 3/2012 | Kovalsky | A61F 2/2418 623/2.11 |
| 2012/0078347 | A1 * | 3/2012 | Braido | A61F 2/915 623/1.26 |
| 2012/0078353 | A1 * | 3/2012 | Quadri | A61F 2/2427 623/2.14 |
| 2015/0157455 | A1 * | 6/2015 | Hoang | A61F 2/2418 264/269 |
| 2018/0078372 | A1 * | 3/2018 | Hill | A61F 2/2409 |
| 2019/0091013 | A1 * | 3/2019 | Alkhatib | A61F 2/2433 |
| 2020/0093597 | A1 * | 3/2020 | O'Connell | A61B 90/39 |
| 2022/0211492 | A1 * | 7/2022 | Pintor | A61F 2/2433 |
| 2022/0257374 | A1 * | 8/2022 | Agreli | A61F 2/2418 |
| 2023/0355382 | A1 * | 11/2023 | Hoang | A61F 2/2418 |
| 2023/0363882 | A1 * | 11/2023 | Dalbow | A61F 2/9522 |
| 2023/0414348 | A1 * | 12/2023 | Maimon | A61F 2/2418 |
| 2024/0024100 | A1 * | 1/2024 | Heniford | A61F 2/2418 |
| 2024/0041595 | A1 * | 2/2024 | Hofferberth | A61F 2/2418 |
| 2024/0156590 | A1 * | 5/2024 | Dorman | A61F 2/2418 |
| 2025/0073023 | A1 * | 3/2025 | Ness | A61F 2/2433 |
| 2025/0339267 | A1 * | 11/2025 | Shitrit | A61L 27/18 |

* cited by examiner

S, Mises
(Avg: 75%)

+1.785e+03
+1.637e+03
+1.489e+03
+1.341e+03
+1.193e+03
+1.045e+03
+8.973e+02
+7.493e+02
+6.013e+02
+4.533e+02
+3.053e+02
+1.573e+02
+9.334e+00

VENOUS VALVE PROSTHESIS

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2021/059287, which was filed Apr. 9, 2021, which application claimed priority from German Application Number 10 2020 110 490.1, which was filed Apr. 17, 2020 and from German Application Number 10 2020 111 388.9, which was filed Apr. 27, 2020.

FIELD OF THE INVENTION

A field of the invention concerns prosthetic venous valves for transporting a flow of body fluid, e.g., blood, in a vessel in a predetermined direction, e.g., toward the heart.

BACKGROUND

A natural venous valve (lat. valvula venosa) is a fold formation of the inner lining (endothelium) of the veins. A venous valve consists of two (rarely three) crescent-shaped leaflets. Venous valves are especially numerous in those veins in which the blood must be transported against the force of gravity (e.g. in the legs). As the blood flows back, the leaflets of the venous valve are captured and close the lumen of the vein. Venous valves thus act like a check valve and ensure that blood flows in only one direction, namely toward the heart. Since blood flow in the veins is predominantly effected by forces acting on the vein from the outside (e.g. contractions of the skeletal muscles, muscle pump), the venous valves ensure that the blood does not flow back in the direction of the periphery, e.g. into the legs, during rest phases.

Defective venous valves can promote the development or progression of chronic venous insufficiency (CVI). One option for therapy is to replace defective natural venous valves surgically, preferably minimally invasively, with venous valve prostheses.

Minimally invasive venous valve prostheses with a stent-like support structure and attached valve leaflets have been described in numerous publications. By way of example, reference is made to the publications U.S. Pat. No. 9,192, 473 B2, U.S. Pat. No. 8,057,532 B2, US 2009/0062907 A1, US 2011/0060405 A1, US 2014/207229 A1, US 2015/ 209246 A1, US 2016/022421 A1, WO 2005/065594 A1, WO 2006/086096 A1. Common to such prior approaches is a stent that serves both as a fixation of the valve leaflets and as a fixation in the vessel. As a result, the stent is only partially sheathed by the skirt.

Known venous valve prostheses have problems in establishing complete valve closure, which usually correlates with undesirable thrombus formation. Thrombus formation occurs primarily in areas of low blood flow or stasis. These areas are found in the leaflet valve pockets, or sinus. Furthermore, previously known prosthetic venous valves show excessive colonization and thus thickening of the leaflet structures, resulting in impaired valve function. In addition, tilting and migration of the support structures is a risk associated with previous prosthetic venous valves.

SUMMARY OF THE INVENTION

A preferred venous valve prosthesis for transporting blood in a vein in a predetermined direction includes a hollow-cylindrical support structure. A skirt is connected to the support structure and forms a closed, circumferential jacket of the support structure. The prosthesis also includes a valve leaflet arrangement with a first valve leaflet and a second valve leaflet, each being connected to the skirt. A downstream edge of the first valve leaflet and a downstream edge of the second valve leaflet are opposite to each other and configured in such a manner that in a first state of the valve leaflet arrangement they form an opening for blood to flow through in the predetermined direction and in a second state of the valve leaflet arrangement the opening is closed and to prevent a backflow of blood in a direction opposite to the predetermined direction. A ratio of the inner diameter of the support structure to its length in the predetermined direction is at most 1

BRIEF DESCRIPTION OF THE DRAWINGS

The invention is explained below by examples of embodiments and with reference to the figures. In this context, all the features described and/or illustrated constitute the subject-matter of the invention, either individually or in any combination, even irrespective of their summary in the claims or their references.

It shows schematically.

DETAILED DESCRIPTION OF THE PREFERRED EMBODIMENTS

Figure 1:
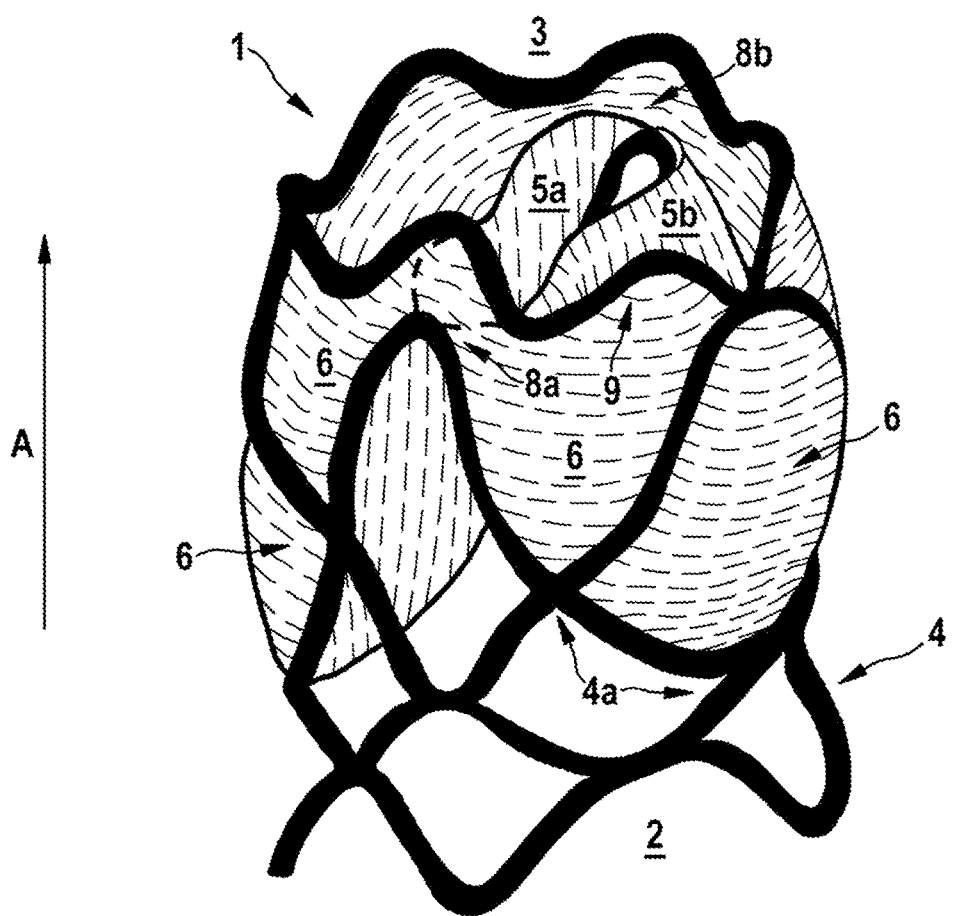
FIG. 1 an example of a venous valve prosthesis according to the invention in a perspective view from the side, FIG. 2 a detail of FIG. 1, FIG. 3 an unwinding of the support structure of the vein valve prosthesis according to FIG. 1, FIG. 4 the venous valve prosthesis according to FIG. 1 in a first state in a Top view, FIG. 5 the venous valve prosthesis according to FIG. 1 during the transition to the second Condition, also in a top view, FIG. 6 a further embodiment of a venous valve prosthesis according to the invention, FIG. 7 an unwinding of the support structure of the prosthetic venous valve shown in FIG. 6, FIG. 8 a perspective view of the support structure or venous valve prosthesis shown in FIGS. 6 and 7 with a valve leaflet assembly including two valve leaflets, FIG. 9 a view of a simulation of a crimped support structure in the manner of FIGS. 6 to 8, FIG. 10 a view of a simulation of an expanded support structure implanted in a vessel in the manner of FIGS. 6 to 8, FIG. 11 a perspective view of a further embodiment of a venous valve prosthesis according to the invention, FIG. 12 a perspective view of a further embodiment of a venous valve prosthesis according to the invention, FIG. 13 a perspective view of a further embodiment of a venous valve prosthesis according to the invention with additional anchoring brackets, and FIG. 14 a perspective view of a venous valve prosthesis according to a further aspect of the invention with additional anchoring brackets.

A prosthetic venous valve (also denoted as venous valve prosthesis) of the invention can avoid thrombus formation and reduce colonization and thickening of the leaflets. Furthermore, the risk of tilting or migration of the implant can be reduced. A preferred venous valve prosthesis according to the invention has a (e.g. substantially hollow-cylindrical, in particular hollow-cylindrical) support structure, which may be formed by interconnected struts, which may be configured such that, in the implanted state, they lie against the inner side of the vessel of the vein to be treated over most of their length, a skirt (also referred to as a jacket or sheath), the skirt being connected to the support structure and forming a closed sheath along the support structure, and a first valve leaflet and a second valve leaflet, which are each connected to the skirt. A downstream edge of the first valve leaflet and a downstream edge of the second valve leaflet are in particular freely opposed to each other and are arranged such that in a first state of the valve leaflet arrangement an opening is formed for blood to flow therethrough in the predetermined direction and in a second state of the valve leaflet arrangement the opening is closed and thus blood is prevented from flowing back in the direction opposite to the predetermined direction.

According to one embodiment of the invention, a first end of each of the downstream edge of the first valve leaflet and the second valve leaflet are connected to each other and to a vertex of a first arcuate strut of the support structure. A second end of each of the downstream edge of the first valve leaflet and the second valve leaflet are also connected to each other and to an apex of a second arcuate strut of the support structure, the first arcuate strut and the second arcuate strut facing each other in a direction transverse to the predetermined direction and being movable (together with the first and second ends of said edges of the first and second valve leaflets attached thereto) in a direction transverse to the predetermined direction such that, upon a pressure-induced increase in the internal diameter of the vessel or vein, a transition from the first state to the second state is accomplished. vein, a transition from the first state to the second state of the valve leaflet arrangement is accomplished.

The above embodiment of the venous valve prosthesis according to the invention has the advantage of reducing thrombus formation in that, when the internal pressure in the vessel is low to medium or the internal diameter of the vessel is small to medium, the valve leaflet assembly assumes the first state, i.e., the first and second valve leaflets form an opening between them so that blood can flow through the venous valve prosthesis in the predetermined direction. The predetermined direction corresponds to an axial or longitudinal direction of the support structure. The flow of blood through the prosthetic venous valve is realized regardless of the existing flow rate of blood through the prosthetic venous valve. This means that an opening is formed between the first valve leaflet and the second valve leaflet even if the flow rate is small. According to recent findings, flow vortices are formed in the area downstream of the first and second valve leaflets due to the flow of blood through the prosthetic venous valve, so that this area is also flowed through by the blood, thereby preventing thrombus formation. Thus, the times during which the second state of the valve leaflet assembly is assumed, i.e., the orifice is closed and stasis occurs, are extremely short and limited to the presence of high internal pressure in the vessel. In the second condition, the high internal pressure in the vessel, for example from an internal overpressure of 30 mmHg, increases the internal diameter. As a result, the arcuate struts and, in particular, their vertices are moved outward transversely to the direction of flow or the axial direction of the support structure, i.e., for example, in a radial direction with respect to the support structure. This movement is also performed by the first and second ends of the edges of the valve leaflets, which are attached to the apex of the respective arcuate strut, i.e. the ends of the edges of the valve leaflets are also moved outward in the radial direction. This causes the downstream edges of the opposing first and second valve leaflets to tighten and close. The valve leaflet assembly assumes the second state, in which backflow of body fluid in the direction opposite to the predetermined direction (for example, in a direction away from the heart) is prevented. As the pressure increases, the inner diameter of the vessel increases, resulting in tighter closure of the prosthetic venous valve. A further increase in pressure leads to a further increase in the closing force of the valve leaflets. Thus, in this embodiment, the prosthetic venous valve according to the invention, i.e., its opening and closing, is pressure-controlled and self-regulating.

The embodiment of the prosthetic venous valve is based in particular on utilizing the physiological change in diameter of a vessel, which occurs due to the very high compliance of the vessel wall, for example in veins, to pressure changes inside the vessel, for closing the opening between the two valve leaflets that exists in the initial state. In one embodiment, the valve leaflet arrangement is set up in such a way that, after implantation in a vessel, the second state is assumed at an overpressure in the vessel relative to outside the vessel of about 30 mmHg (=3.9997 kPa).

In one embodiment of the invention, the first valve leaflet and the second valve leaflet have a semicircular or lunar geometry. In one embodiment example, the respective downstream free edge of the first valve leaflet and the second valve leaflet is about 15% to 30% larger, preferably 20% to 30% larger, than the inner diameter of the support structure. In this embodiment example, a secure closure of the prosthetic venous valve at a high internal pressure and a defined opening of the prosthetic venous valve are achieved.

In another embodiment, the first arcuate strut and the second arcuate strut are not connected to the downstream adjacent strut row. This results in better radial mobility of the first and second arcuate struts in the event of a change in diameter of the vessel, and thus in reliable closure of the valve leaflets in the event of a significant increase in the internal pressure of the vessel.

In one embodiment, the first arcuate strut and the second arcuate strut are formed such that their respective apex points in the predetermined direction (flow direction). This means that the sections of the respective arcuate structure connected to the apex are further upstream than the apex.

In a further embodiment of the invention, the entire edge of the first valve leaflet and the second valve leaflet, which is not downstream and exposed, are each connected to the arcuate strut. This effectively prevents blood from flowing past the prosthetic venous valve.

In a further embodiment, the first arcuate strut and the second arcuate strut are connected to each other via a substantially elliptical, in particular elliptical, structure of the support structure. The elliptical structure is formed by further struts of the support structure and the first and second arcuate struts. In this case, the elliptical structure does not run in a plane, but is curved three-dimensionally as a whole. In particular, the first and second arcuate struts form ends of the elliptical structure that are bent in the predetermined direction. In one embodiment, the support structure has a plurality of further struts extending obliquely with respect to the elliptical structure. In one embodiment, the elliptical structure forms the upstream edge of the skirt. For example, the skirt is attached to the elliptical structure with its upstream edge.

In one embodiment, the support structure has a plurality of diamond-shaped cells formed by the struts. The struts are attached to each other at nodes.

In a further embodiment, the row of struts adjacent to the first and second arcuate struts, for example the row of struts located downstream adjacent to the first and second arcuate struts, has an undulating shape. The support structure therefore adapts particularly well to different vessel shapes.

In a further embodiment, the downstream adjacent strut row runs in such a waveform that it is parallel to the first arcuate strut in the region of the apex of the first arcuate strut and parallel to the second arcuate strut in the region of the apex of the second arcuate strut. The apex of the first arcuate strut and the apex of the adjacent row of struts parallel thereto are preferably at a distance of between 0.5 mm and 15 mm. This ensures good mobility of the first and second arcuate struts in the radial direction.

In one embodiment of the invention, tilting of the prosthetic venous valve can be prevented by the ratio of the inner diameter of the support structure to its length in the predetermined direction (axial direction) being at most 1.

In another embodiment, the support structure has a superelastic alloy with shape memory property, for example NiTi (nickel-titanium, nitinol) or NiTiCu (nickel-titanium-copper). Superelastic alloys means alloys exhibiting superelasticity, also called pseudoelasticity. Superelasticity is the property of a material (in this case an alloy) to return to its original shape without being plastically deformed when the load is removed after deformation. Superelasticity is based on a reversible transformation of the crystal structure. While shape memory properties refer to a thermal shape memory of a material, superelasticity refers to a mechanical shape memory of a material.

In another embodiment, the skirt and/or the first and second valve leaflets may use a xenogeneic material, for example, porcine or bovine pericardium, a processed material, for example, at least one material selected from the group consisting of bacterial cellulose, processed pericardium, polymeric nanofiber nonwoven, polymeric film material, and fiber composites.

In one embodiment, the first and second valve leaflets and/or the skirt can be attached to the support structure by sewing, gluing or contact welding. In this way, a particularly secure and tight connection between the support structure and skirt or the first and second valve leaflets can be achieved.

According to a further embodiment of the venous valve prosthesis according to the invention, it is provided that the support structure extends along an axis (in particular longitudinal axis) which coincides with the predetermined direction of blood transport, wherein the support structure further includes a first ring structure which surrounds an inflow region of the venous valve prosthesis, as well as a second ring structure spaced therefrom which surrounds an outflow region of the venous valve prosthesis, wherein the second ring structure lies opposite the first ring structure in the predetermined direction or in the direction of the axis, and wherein the two ring structures are connected by longitudinal connectors extending along the axis. in the direction of the axis, and wherein the two ring structures are interconnected by longitudinal connectors extending along the axis. Longitudinal connectors are understood to be struts whose length in the axial direction is a multiple (at least twice) of the axial length of the struts of the ring structure.

Further, according to one embodiment of the invention, the first ring structure includes a plurality of circumferentially interconnected cells, each cell of the first ring structure being formed by interconnected struts. Further, according to one embodiment of the invention, the second ring structure includes a plurality of circumferentially interconnected cells, each cell of the second ring structure being formed by interconnected struts.

The struts can have a width (in the circumferential direction of the support structure) of 0.1 mm, for example, and a wall thickness (in the radial direction of the support structure) of 0.140 mm, for example.

Preferably, the struts or the cells are integrally connected, e.g. by cutting the support structure from a tubular blank consisting of a metal alloy by laser cutting. All other connections between struts or elements of the support structure are also preferably integrally designed, i.e. e.g. in one piece or as a homogeneous structure.

For example, the support structure can be made from a tubular blank of a nickel-titanium shape memory alloy, e.g. nitinol, in particular laser cut. A support structure behaves accordingly superelastically (see also above) and can be crimped to a diameter of 1.35 mm (4 Fr), for example, without significant permanent plastic strain. The surface of the support structure can be electropolished.

According to a preferred embodiment of the invention, it is provided that the first ring structure is formed of eight to twelve cells, preferably ten cells, which are interconnected in the circumferential direction of the support structure. Furthermore, according to an embodiment of the invention, it is provided that the second ring structure is formed of eight to twelve cells, preferably ten cells, which are interconnected in the circumferential direction of the support structure.

Furthermore, according to a preferred embodiment of the invention, it is provided that the support structure can be transferred from a compressed or crimped state, in which the prosthetic venous valve can be implanted in the vein or vessel, to an expanded state, in which the support structure can be anchored in the vein or vessel. In particular, the support structure may be designed to be self-expandable. For this purpose, the support structure can, for example, be formed from a suitable nickel-titanium alloy (e.g. nitinol, see also above).

Furthermore, according to one embodiment of the invention, it is provided that the cells are diamond-shaped with respect to the expanded state of the support structure, so that in particular the respective ring structure forms two meander-shaped or zigzag-shaped edge regions running in the circumferential direction.

According to one embodiment of the prosthetic venous valve, the two ring structures may be configured to anchor the prosthetic venous valve in the vein.

Preferably, according to one embodiment of the invention, the first and second ring structures are interconnected by a first and a second longitudinal connector, and preferably integrally (see above), wherein each longitudinal connector is arcuate, preferably parabolic, with respect to an imaginary unwound state of the support structure in which the support structure extends two-dimensionally in a plane, and thereby has a vertex region and two ends.

Here, it is preferably provided that the apex region of the respective longitudinal connector is connected to the first ring structure (and preferably integrally, see above), and that the two ends of the respective longitudinal connector are connected to the second ring structure (preferably also integrally), wherein in particular the apex region of the respective longitudinal connector adjoins a tip of a cell of the first ring structure facing the second ring structure.

Furthermore, according to a preferred embodiment of the invention, it is provided that each end of the first longitudinal connector is brought together with an associated end of the second longitudinal connector and is thereby connected (preferably integrally) to the second annular structure via a common connection region, wherein in particular the respective connection region adjoins a tip of a cell of the second annular structure facing the first annular structure.

According to a further embodiment of the prosthetic venous valve, it is provided that the valve leaflet assembly is connected to the support structure via the longitudinal connectors. Preferably, it is further provided that the connecting regions are arranged offset by 90° in the circumferential direction of the support structure relative to the apex regions, i.e., in each case by a quarter of the circumference of the support structure. This allows the valve leaflet arrangement to be supported or shaped in an advantageous manner by the longitudinal connectors, whereby the two downstream edges of the valve leaflets can extend between said connecting regions.

According to a further alternative embodiment of the invention, it is provided that the longitudinal connectors are not formed in an arcuate or parabolic manner in the manner described above, but rather, in the expanded state of the support structure, each arcuately bulge outward in the radial direction of the support structure and are thereby designed to press against an inner vessel wall of the vein for anchoring the prosthetic venous valve. Thus, anchoring is also accomplished here by the longitudinal connectors and primarily not by the ring structures, which are used here to secure the valve leaflet assembly. The valve leaflet arrangement or the valve leaflets are now preferably fixed to the ring structures.

Due to the outwardly curved longitudinal connectors, a space is created in the center of the venous valve prosthesis that is practically free of elements of the support structure, so that impairment of the valve leaflets located there is avoided to the greatest possible extent with advantage. In addition, when the blood flows through the venous valve, flow vortices are formed in this area, so that this area is also flowed through by the blood and thrombus formation is thus avoided.

According to one embodiment, the respective outwardly curved longitudinal connector is connected via a first end to a connecting strut interconnecting two adjacent cells of the first annular structure in the circumferential direction of the support structure, and the respective longitudinal connector is connected via a second end to a connecting strut interconnecting two adjacent cells of the second annular structure in the circumferential direction of the support structure.

According to an alternative embodiment, it is provided that the respective longitudinal connector is connected via a first end to a tip of a (preferably diamond-shaped) cell of the first ring structure facing the second ring structure, and that the respective longitudinal connector is connected via a second end to a tip of a (preferably diamond-shaped) cell of the second ring structure facing the first ring structure.

Furthermore, according to one embodiment of the invention, it is provided that the skirt is fixed to the first ring structure, the skirt being arranged on an outer side and/or on an inner side of the first ring structure. In this case, an upstream edge region of the respective valve leaflet is preferably connected to the skirt.

Furthermore, according to one embodiment of the prosthetic venous valve, it is provided that the skirt and/or the valve leaflets and/or the valve leaflet assembly is formed from at least one of the following materials or includes at least one of the following materials, wherein the respective material is preferably electrospun: a polyurethane (PU), a polycarbonate ethane (PCU) or a copolymer (TSPCU), such as polycarbonate ethane-co-silicone (PCU-co-Si B), a polyurethane-co-silicone (PU-co-Si A), a thermoplastic copolyester elastomer (TPC-ET), expanded polytetrafluoroethylene (ePTFE), polyvinylidene fluoride (PVDF), poly (vinylidene fluoride-co-hexafluoropropylene) (PVDF-co-HFP, engl. Poly(vinylidene fluoride-co-hexafluoropropylene)), polyacrylonitrile (PAN) as well as dual or coaxial electrospun composites or fiber composites of the above materials and, for example, polyvinylpyrrolidone and hyaluronic acid (PVP/HA, absorbable component).

Polymer materials are proving to be suitable for venous valve implants. The sterilizability of surface nonwovens of these materials is advantageous. Furthermore, these polymers can be easily processed by electrospinning. According to one embodiment of the invention, it is provided in this respect that the skirt and/or the valve leaflets are spun directly into the support structure by electrospinning.

Furthermore, the valve leaflet assembly or valve leaflets formed from the aforementioned polymers can be joined with a suitable adhesive, e.g. a silicone sealant (e.g. a silicone rubber, e.g. silicone rubber RS 692-542, RS Components Ltd., Corby, UK) or a fabric adhesive, e.g. fibrin adhesive, by sewing or by contact welding in order to join the valve leaflets or valve leaflet assembly to the support structure.

Expediently, the venous valve prostheses described above have a ratio of inner diameter to length of the support structure of at most 1, preferably less than 1. This prevents tilting of the venous valve prosthesis in the vessel.

Figure 2:
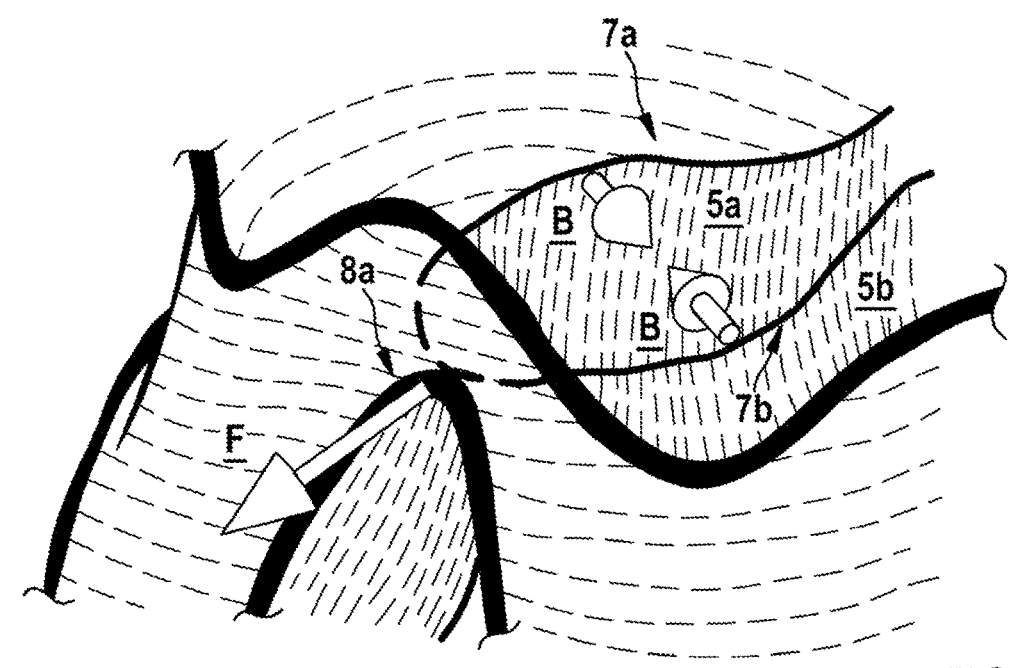
Figure 3:
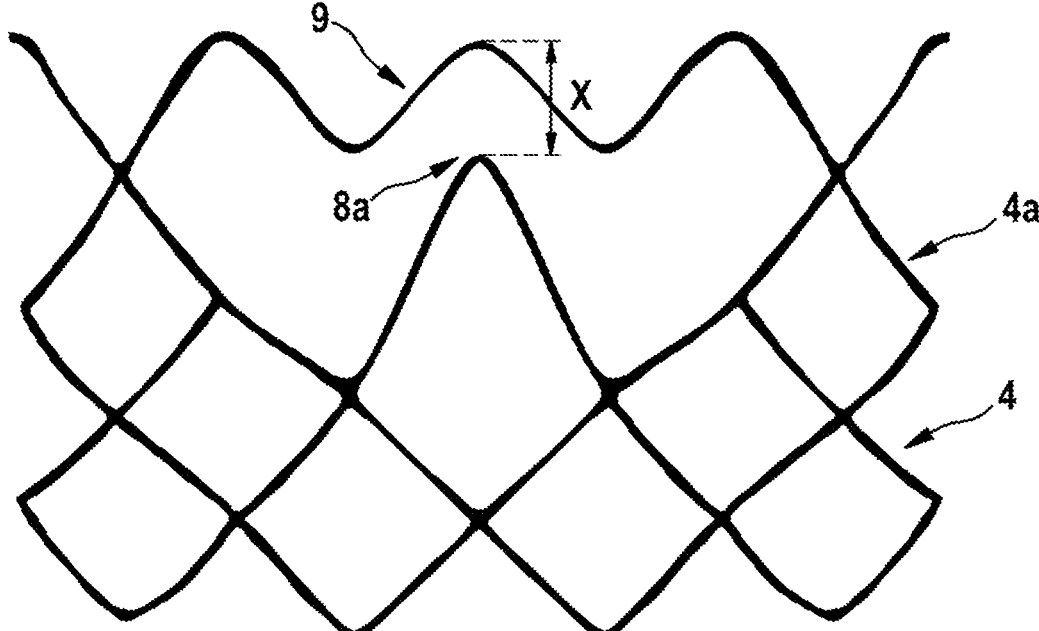

The embodiment example of a venous valve prosthesis 1 shown in FIG. 1, which is shown in detail in FIG. 2 and in an unwinding of a support structure 4 in FIG. 3, is intended for a vessel with an inner diameter of 5 mm to 35 mm. The prosthetic venous valve 1, which after implantation in a vessel of a body (not shown) has a body fluid, preferably blood, flowing through it from its first end 2 to its second end 3 in the predetermined direction, has the support structure 4 with a plurality of struts 4a to which a first valve leaflet 5a and a second valve leaflet 5b and a skirt 6 are attached. The skirt 6 is attached to the support structure 4 on the downstream sides of the two valve leaflets 5a, 5b. The direction of flow of the body fluid, which is parallel to the longitudinal axis of the support structure, is indicated in FIG. 1 by the arrow A The material for the support structure 4 may be a superelastic alloy with shape memory properties, such as nitinol. The material for the skirt 6 may be xenogenic materials, such as porcine or bovine pericardium, further processed materials, such as bacterial cellulose or processed pericardium, or artificial materials, such as polymer-based nanofibrous webs. Support structure 4 and skirt 6 may be joined by sewing, gluing, contact welding, or other technologies.

To avoid tilting of the vein valve prosthesis 1, it is advantageous if the ratio of the inner diameter to the length of the support structure 4 is at most 1.

Figure 5:
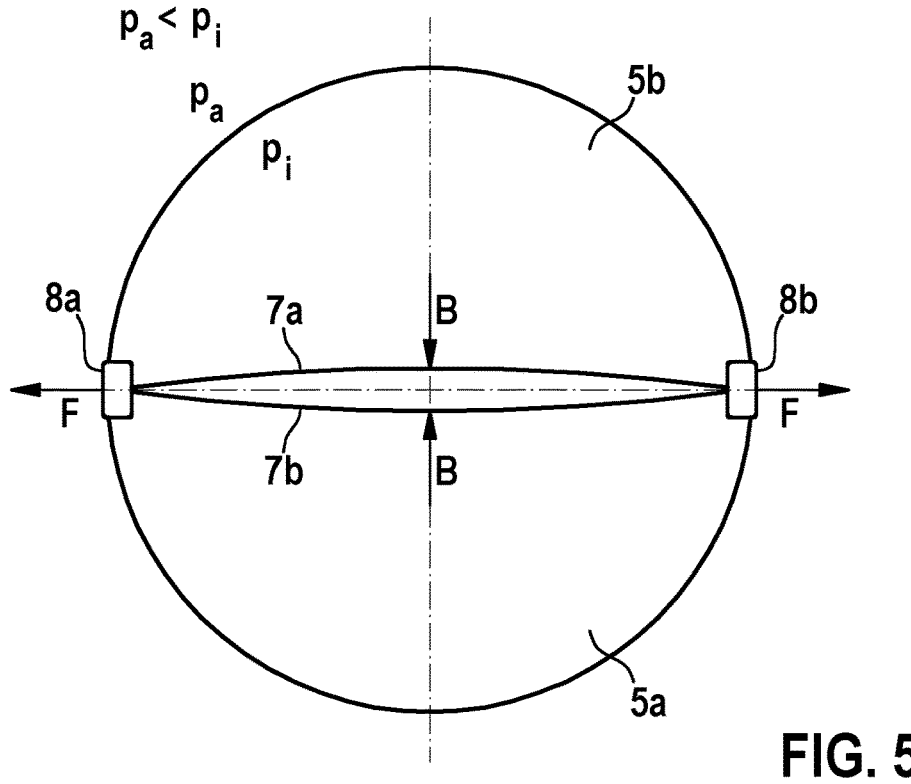

When closed (FIG. 5 shows the valve leaflets 5a, 5b shortly before closure), the two valve leaflets 5a, 5b together with the skirt 6 forming a mantle form the shape of a sine. The ends of the downstream free edges 7a, 7b of the first valve leaflet 5a and the second valve leaflet 5b are each attached to a vertex of the opposing strut arcs (arc-shaped struts) 8a, 8b. These strut arches 8a, 8b are not connected to the adjacent strut row 9 in the direction of the second end 3. Between the strut arches 8a, 8b and the adjacent strut row 9 is the skirt 6 which seals the prosthetic venous valve 1 together with the valve leaflets 5a, 5b attached to the extended strut arches 8a, 8b so that no body fluid or blood can flow past.

The distance X of the strut arcs 8a, 8b from the adjacent strut row 9 in the direction of the longitudinal axis of the support structure 4 is preferably between 0.5 mm and 15.0 mm. This is shown in FIG. 3. Here, as shown in FIG. 3, the adjacent strut row 9 runs parallel to the strut arcs 8a, 8b in the region of the apex of the strut arcs 8a, 8b—namely in a wave form.

The two strut arches 8a, 8b are thus movable radially (i.e. transversely to the longitudinal axis of the support structure 4 or to the direction of flow (see arrow A)). Due to the bicuspid design, the free edges 7a, 7b of the two valve leaflets 5a, 5b are brought together by an inward movement (see arrows B in FIG. 2) when the two opposing strut arcs 8a, 8b move apart in the radial direction due to a force F. The two strut arcs 8a, 8b move radially. This is shown in FIGS. 2 and 5.

Figure 4:
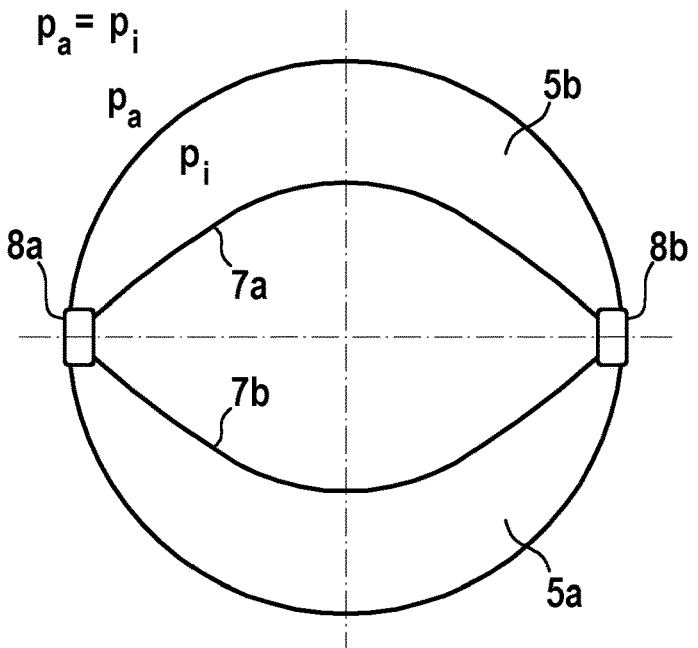

The prosthetic venous valve 1 is designed in such a way that it has an open state as its starting position (see FIG. 4). The initial position is characterized by the fact that no pressure or only a low pressure loads the prosthetic venous valve 1 or the vessel in which the prosthetic venous valve is inserted. This results, for example, when the internal pressure i is equal or approximately equal to the external pressure a. For example, the pressure difference between the internal pressure i and the external pressure a is below 30 mmHg. The closing of the prosthetic venous valve 1, i.e. the transition from the first state defined above to the second state defined above, occurs as a result of a pressure load, for example in the form that the inner pressure i in the vessel is greater than the outer pressure a, whereby the vessel and with the vessel the support structure 4 inserted into the vessel expands as a result of the pressure increase and thereby a radially outwardly directed force F is exerted on the strut arches 8a, 8b. For example, the pressure difference between the internal pressure i and the external pressure a is equal to or greater than 30 mmHg. The movement of the strut arches 8a, 8b is finally converted into a movement B of the ends of the free, downstream edges 7a, 7b of the valve leaflets 5a, 5b attached to the strut arches 8a, 8b, and thus of the entire valve leaflets 5a, 5b, resulting in leaflet closure. The greater the force F acting on the strut arches 8a, 8b, the more strongly the edges 7a, 7b of the valve leaflets 5a, 5b are pressed against each other and the valve closure is reinforced. This effect is referred to as pressure control. The function of the valve prosthesis 1 should be designed for a pressure of at least 200 mmHg, and the valve closure (i.e., the second state of the valve leaflet assembly) preferably starts at an internal overpressure (i-a) of 30 mmHg, as described above. The distance covered by a strut arch 8a, 8b during radial movement until closure of the valve leaflets 5a, 5b is, for example, at least 7.5%, preferably at least 10%, of the initial diameter of the prosthetic vein valve 1, in order to achieve a defined opening of the prosthetic vein valve 1 on the one hand and a secure closure of the prosthetic vein valve 1 on the other hand.

The internal pressure pi within the prosthetic venous valve 1 is created, for example, by the hydrostatic load when the patient stands up.

The prosthetic venous valve 1 is opened either by a heart-directed blood flow flowing proximally into the first end 2 of the prosthetic venous valve 1 and forcing the two valve leaflets 5a, 5b apart or by the pressure at the distal end 3 of the prosthetic venous valve 1 dropping, causing the prosthetic venous valve 1 to contract and the strut arches 8a, 8b to move inward. As a result, the valve leaflets 5a, 5b form an opening between themselves again and the valve leaflet assembly resumes the first state (initial state).

Figure 6:
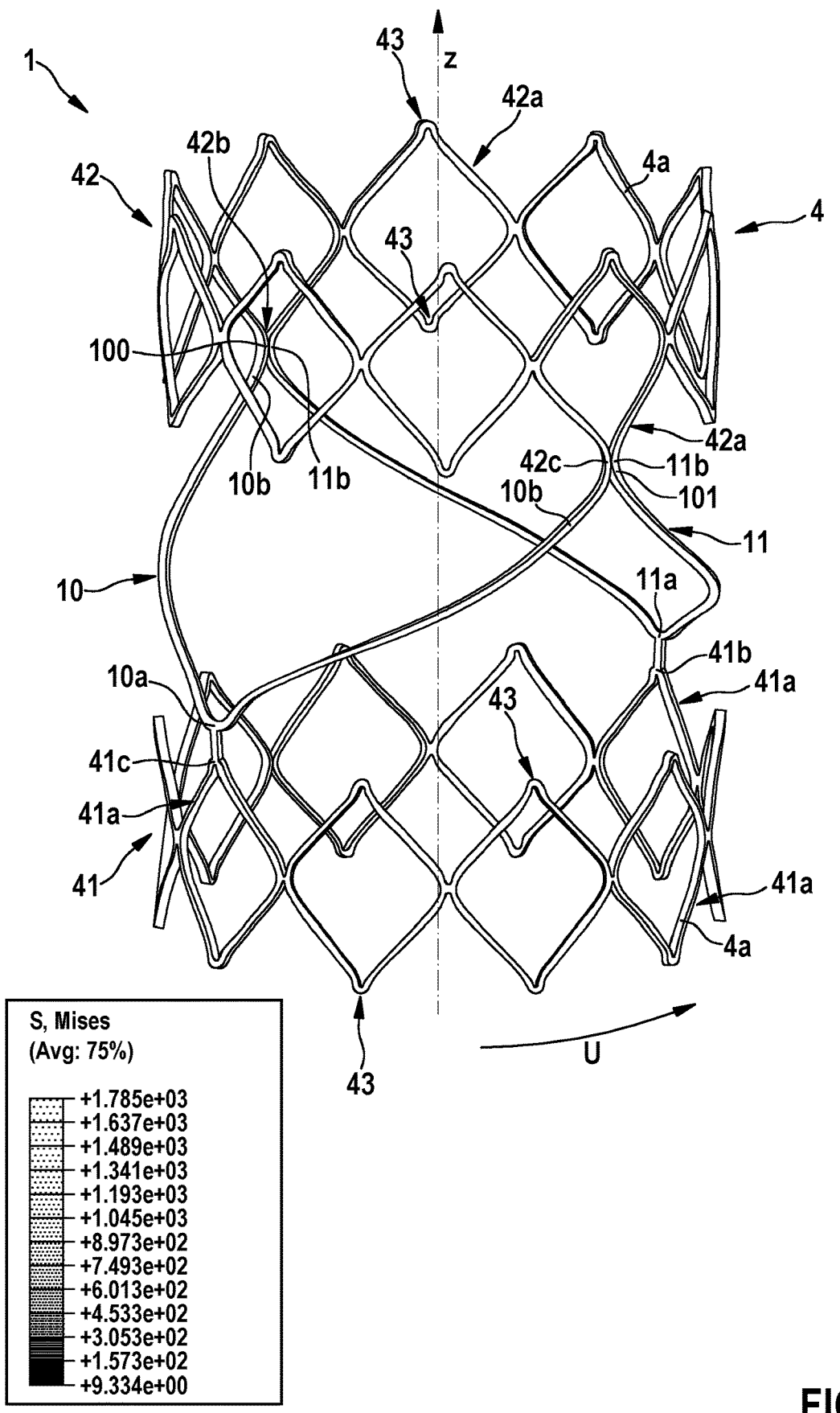

FIG. 6 shows, in connection with FIGS. 7 to 10, a further embodiment of a venous valve prosthesis 1 according to the invention for transporting blood in a vein in a predetermined direction z. The prosthesis 1 has a support structure 4 which runs around in a circumferential direction U, and a skirt 6 which is connected to the support structure 4 and forms a closed jacket in the circumferential direction U of the support structure 4. Furthermore, the prosthetic venous valve 1 includes a valve leaflet arrangement with a first valve leaflet 5a and a second valve leaflet 5b (cf. e.g. FIG. 8), which are each connected to the skirt 6, wherein a downstream edge 7a of the first valve leaflet 5a and a downstream edge 7b of the second valve leaflet 5b are opposite one another and are arranged in such a way that, in a first state of the valve leaflet arrangement, they form an opening for blood to flow through in the predetermined direction z and, in a second state of the valve leaflet arrangement, the opening is closed and thus a backflow of blood in the direction opposite to the predetermined direction z is prevented. The first state of the valve leaflet arrangement is produced by forcing blood through the opening formed between the valve leaflets 5a, 5b due to a pressure provided by the musculature of the person, wherein the valve leaflets close in the backflow direction due to the gravity pressure of the blood or a rapid increase in the gravity pressure of the blood, for example, due to a change in the position of the patient by standing up, which corresponds to the second state.

The support structure 4 can be transferred from a compressed state, in which the prosthetic venous valve 1 can be implanted in a vein, to an expanded state, in which the support structure 4 can be anchored in the vein. In the compressed or crimped state, the support structure 4 has a smaller outer diameter in the radial direction R than in the expanded state. Preferably, the support structure 4 is a self-expandable support structure 4 that moves automatically from the compressed state to the expanded state, provided that no external force acts on the support structure 4 to prevent this expansion.

As can be seen from FIG. 6, the support structure 4 extends along an axis z parallel to the predetermined direction, the support structure 4 furthermore having a first annular structure 41, which surrounds an inflow region of the venous valve prosthesis 1, and a second annular structure 42, which is spaced apart therefrom and surrounds an outflow region of the venous valve prosthesis 1, the second annular structure 42 lying opposite the first annular structure 41 in the direction of the axis z. The two ring structures 41, 42 are connected to one another by longitudinal connectors or struts 10, 11 running along the axis z, the support structure 4 having, in a section lying between the two ring structures 41, 42 and formed by the longitudinal connectors 10, 11, a shape or structure different from the ring structures 41, 42 (in particular with a lower strut density).

The two ring structures 41, 42 each have a plurality of cells 41a, 42a which are interconnected in the circumferential direction U and (in the case of an expanded support structure) are preferably diamond-shaped, the cells 41a, 42a each being formed by interconnected struts 4a of the support structure 4. In the embodiment shown in FIG. 6, the respective ring structure 41, 42 preferably has ten cells 41a, 42a, which are each arranged next to one another in the circumferential direction U Due to the rhombic shape of the cells 41*a*, 42*a*, the ring structures 41, 42 each have two meandering edge regions 43 running in the circumferential direction U in an expanded support structure 4. The ring structures 41, 42 serve to anchor the prosthesis 1 at the target location in the vessel and are particularly suitable for this purpose due to their shape, which guarantees good flexibility and restoring force.

Figure 7:
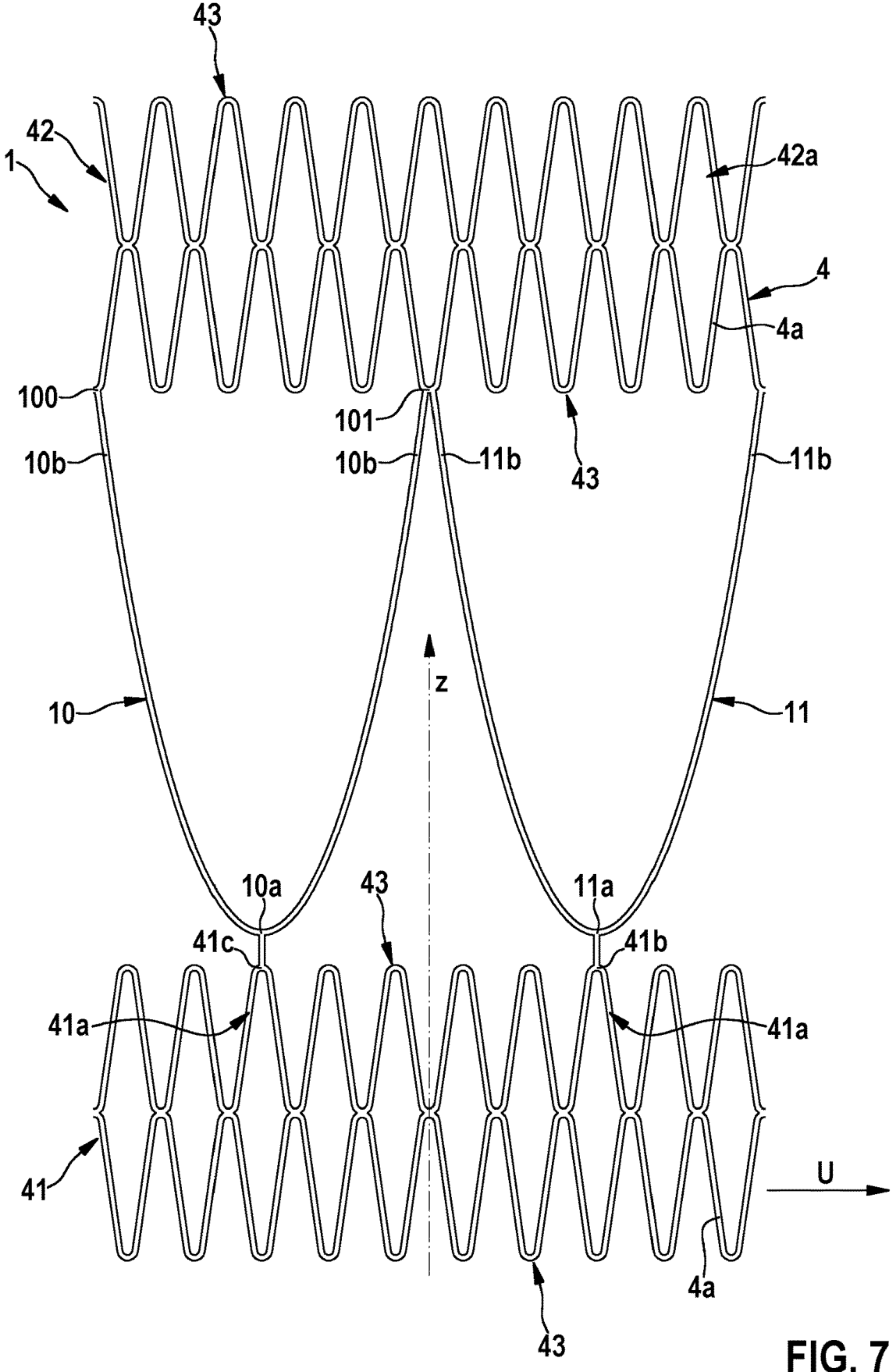

As can be seen from FIG. 6 and in particular from FIG. 7, which shows an unwinding of the support structure 1, the two ring structures 41, 42 are connected to one another by a first and a second longitudinal connector 10, 11, and preferably integrally, each longitudinal connector 10, 11 (with reference to the unwound state of the support structure 4 shown in FIG. 7, in which the support structure 4 extends two-dimensionally in a plane) being of arcuate, preferably parabolic, design. The respective longitudinal connector 10, 11 has an apex region 10*a* and 11*a*, respectively, and two ends 10*b* and 11*b*, respectively.

Preferably, the apex region 10*a*, 11*a* of the respective longitudinal connector 10, 11 is now connected to the first annular structure 41, and preferably integrally, whereas the two ends 10*b* of one longitudinal connector 10 are connected to the second annular structure 42, as are the two ends 11*b* of the other longitudinal connector 11, and preferably integrally in each case.

As can be seen further from FIGS. 6 and 7, it is preferably provided that the apex regions 10*a*, 11 *a* of the longitudinal connectors 10, 11 each adjoin a tip 41*b*, 41*c* of a cell 41*a* of the first annular structure 41 facing the second annular structure 42, the two tips 41*b*, 41*c* being opposite one another transversely to the axis z and in particular being 180° apart in the circumferential direction U (as can be seen in particular from the development according to FIG. 7).

Furthermore, each end 10*b* of the first longitudinal connector 10 is preferably connected to an associated end 11*b* of the second longitudinal connector 11, in each case creating a common connecting region 100, 101 which is connected (preferably integrally) to the second annular structure 42, in particular the respective connecting region 100, 101 adjoining a tip 42*b*, 42*c* of a cell 42*a* of the second annular structure 42 facing the first annular structure 41. In this case, the two connecting regions 100, 101 lie opposite one another transversely to the axis z and, in particular, lie 180° apart in the circumferential direction U (cf. development according to FIG. 7), the connecting regions 100, 101 furthermore being arranged offset by 90° in the circumferential direction U of the supporting structure 4 with respect to the apex regions 10*a*, 11 *a* of the longitudinal connectors.

Figure 8:
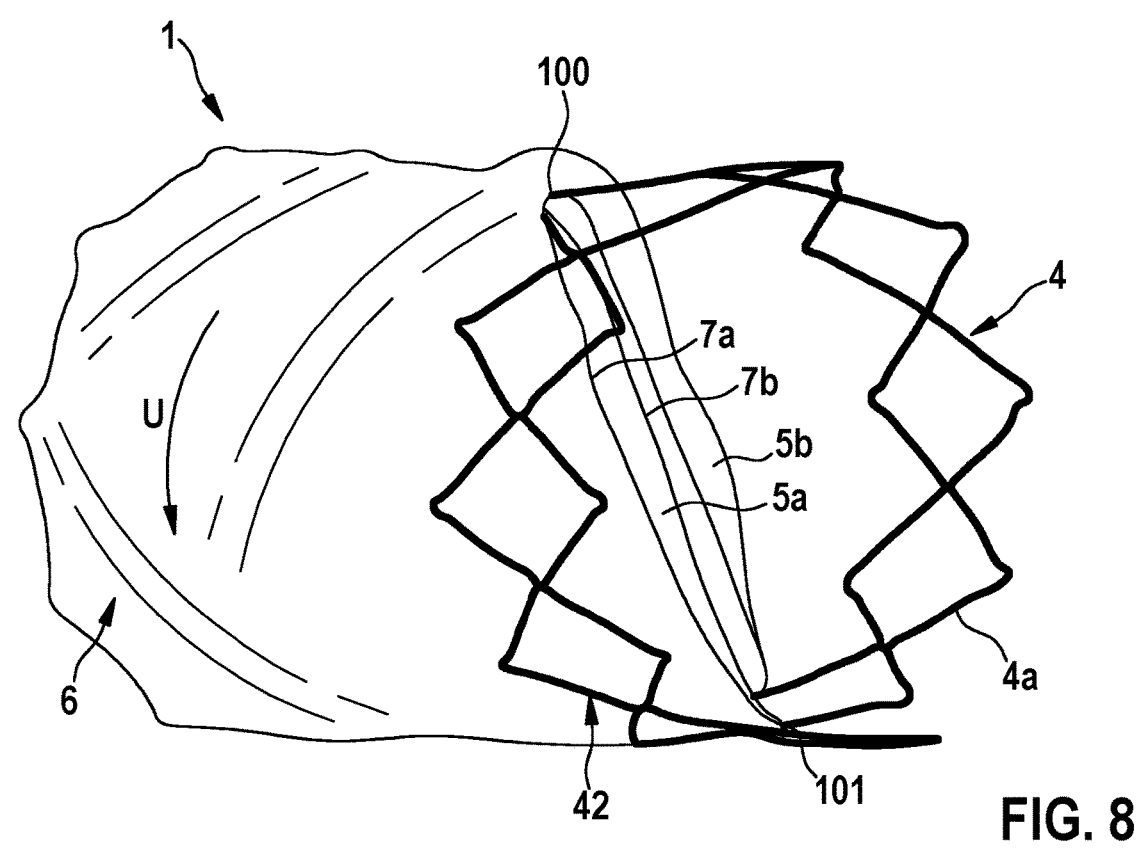

The longitudinal connectors 10, 11 shown in FIGS. 6 and 7 further serve to connect the valve leaflets 5*a*, 5*b* to the supporting structure 4, wherein, according to FIG. 8, the two downstream edges 7*a*, 7*b* of the valve leaflets 5*a*, 5 extend in particular between the connecting regions 100, 101 or are stretched between these connecting regions 100, 101 of the supporting structure 4.

As can further be seen from FIG. 8, the skirt 6 is fixed to the first ring structure 41, whereby the skirt 6 is presently arranged on an outer side of the ring structure 41, but can also extend on the inner side of the first ring structure 41. The upstream edge regions of the respective valve leaflet 5*a*, 5*b* are preferably connected to the circumferential skirt 6.

The skirt 6 and/or the valve leaflets 5*a*, 5*b* can, for example, be made of the materials set out above, in particular electrospun. Particularly suitable or preferred materials for this purpose are, for example. Polyurethane (PU), a polycarbonate ethane (PCU) or a copolymer (TSPCU), such as polycarbonate ethane-co-silicone (PCU-co-Si B), a polyurethane-co-silicone (PU-co-Si A), a thermoplastic copoly-ester elastomer (TPC-ET), expanded polytetrafluoroethyl-ene (ePTFE), polyvinylidene fluoride (PVDF), poly (vinylidene fluoride-co-hexafluoropropylene) (PVDF-co-HFP, engl. Poly(vinylidene fluoride-co-hexafluoropropylene)), polyacrylonitrile (PAN) as well as dual or coaxial electrospun composite or fiber composite materials made of the aforementioned materials and, for example, polyvinylpyrrolidone and hyaluronic acid (PVP/HA, absorbable component).

Figure 9:
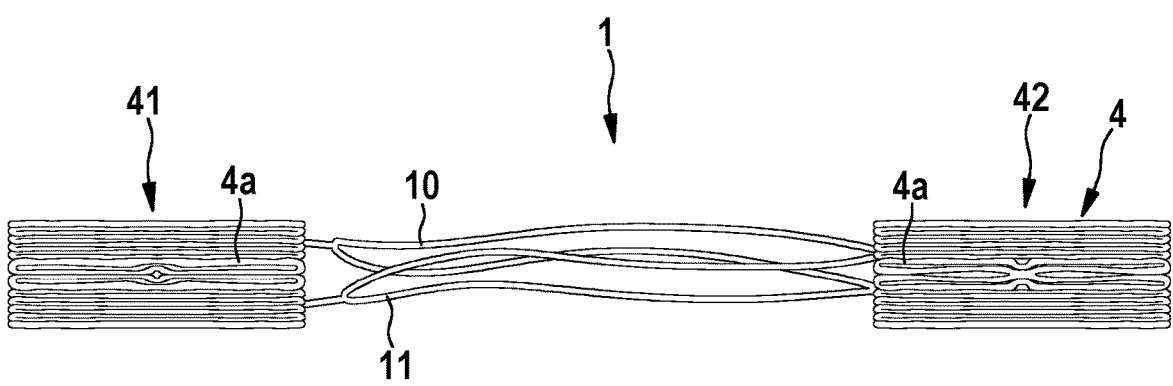
Figure 10:
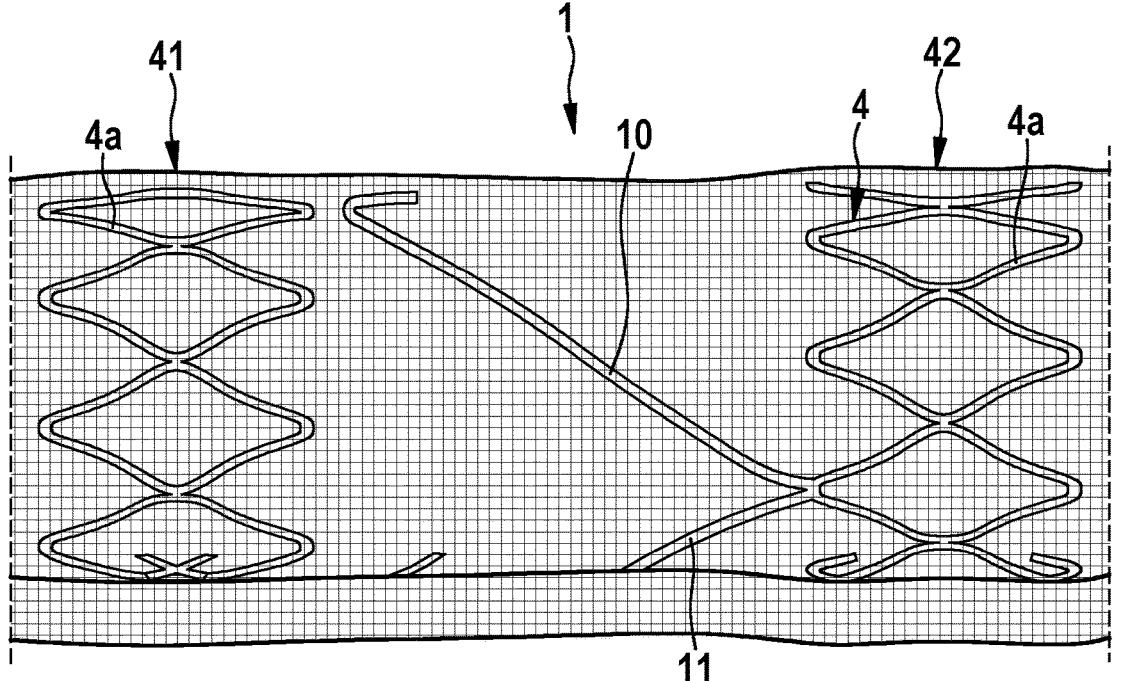

FIG. 9 and FIG. 10 show numerical structural simulations of the stent frame 4 shown in FIGS. 6 to 8, where FIG. 9 shows the load case of the crimped or compressed stent frame 4, whereas FIG. 10 shows the load case of the stent frame 4 inserted into a vessel.

Figure 11:
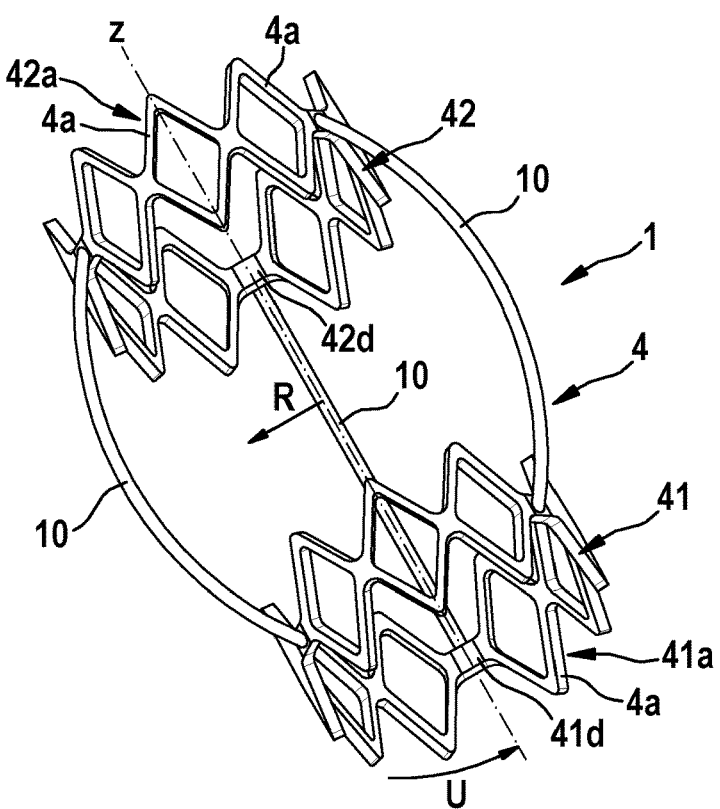

FIG. 11 shows a further embodiment of a venous valve prosthesis according to the invention, wherein here, in contrast to FIG. 6, the two ring structures 41, 42 are connected to one another by longitudinal connectors 10 running along the axis z (e.g. by three longitudinal connec-tors 10), which are each arched outwards in the radial direction R of the supporting structure 4 relative to the expanded state of the supporting structure 4 and are designed to press against an inner vessel wall of the vein for anchoring the venous valve prosthesis 1. In contrast to the embodiment according to FIG. 6, here the central section of the prosthesis 1 defined by the longitudinal connectors 10 serves to anchor the prosthesis 1 in the relevant vessel. The valve leaflet arrangement with the two leaflets 5*a*, 5*b* may be fixed to the two ring structures 41, 42.

Preferably, according to FIG. 11, it is further provided that the respective longitudinal connector 10 is connected via a first end to a connecting strut 41*d* interconnecting two adjacent cells 41*a* of the first annular structure 41, and via a second end to a connecting strut 42*d* interconnecting two adjacent cells 42*a* of the second annular structure 42.

Figure 12:
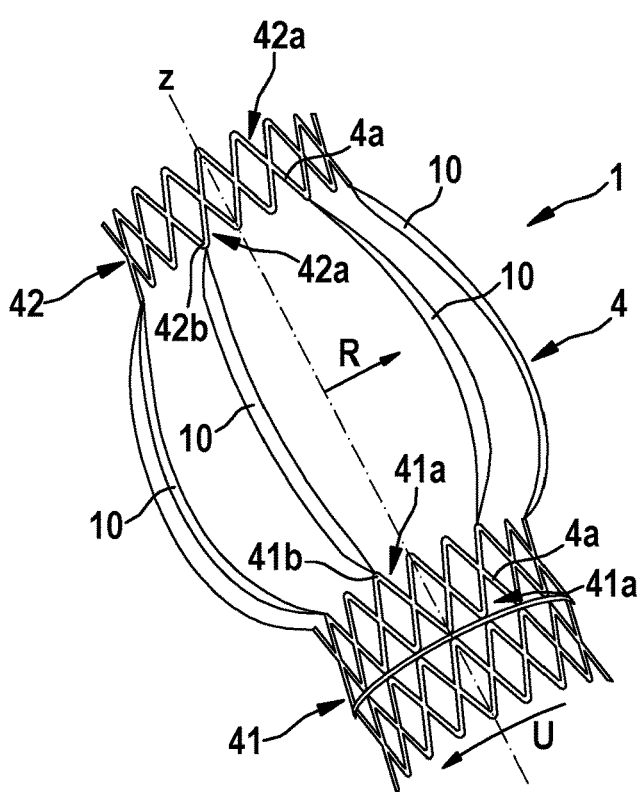

According to an alternative embodiment shown in FIG. 12, in contrast, it is provided that the respective longitudinal connector 10 is connected via a first end to a tip 41*b* of a cell 41*a* of the first ring structure 41 facing the second ring structure 42, and that the respective longitudinal connector 10 is connected via a second end to a tip 42*b* of a cell 42*a* of the second ring structure 42 facing the first ring structure 41. The first annular structure 41 surrounding the inflow region of the prosthesis 1 may be formed longer along the axis x than the second annular structure 42 and may have, for example, more than one row of diamond-shaped cells 41*a*.

Figure 13:
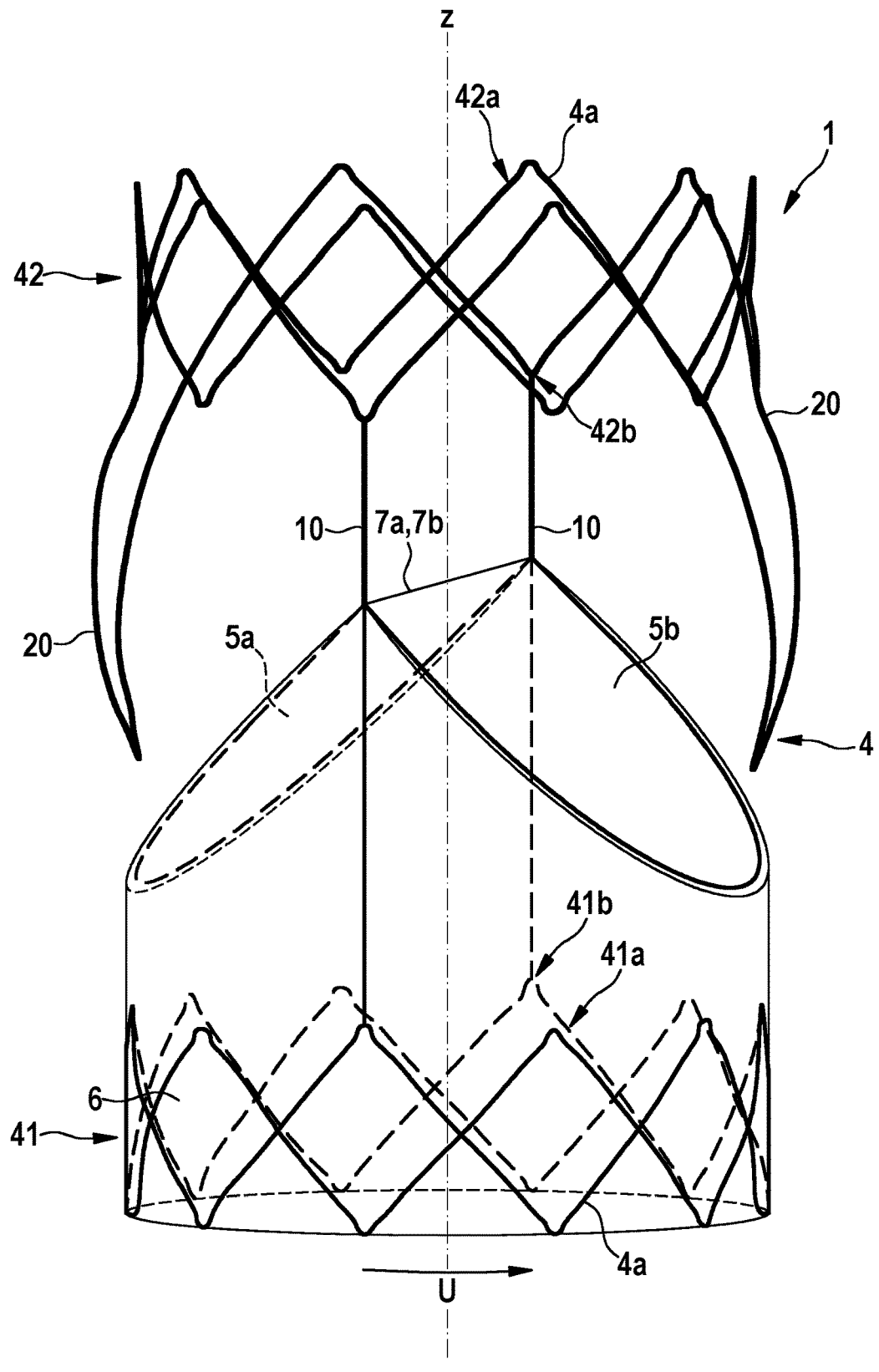

Furthermore, according to the embodiment of a venous valve prosthesis 1 shown in FIG. 13, it may be provided that for better contact with the vessel wall of the vein and for modeling a sinus, the support structure 4 has additional anchoring brackets 20 which project from the second ring structure 42 in the direction of the first ring structure 41, but the free ends of the anchoring brackets 20 are not connected to the first ring structure 41 but are spaced apart from it. Again, the two ring structures 41, 42 may each consist of ten cells 41*a*, 42*a* and are connected to each other by longitu-dinal connectors 10 extending longitudinally along the axis z, which in the shown expanded state of the support structure 4 may in particular extend parallel to each other, and which in particular correspond to the commissure of the valve leaflets 5*a*, 5*b* fixed to the longitudinal connectors 10. According to FIG. 13, the skirt 6 may join or be connected to the valve leaflets 5*a*, 5*b* on the inner side of the first annular structure 41.

Figure 14:
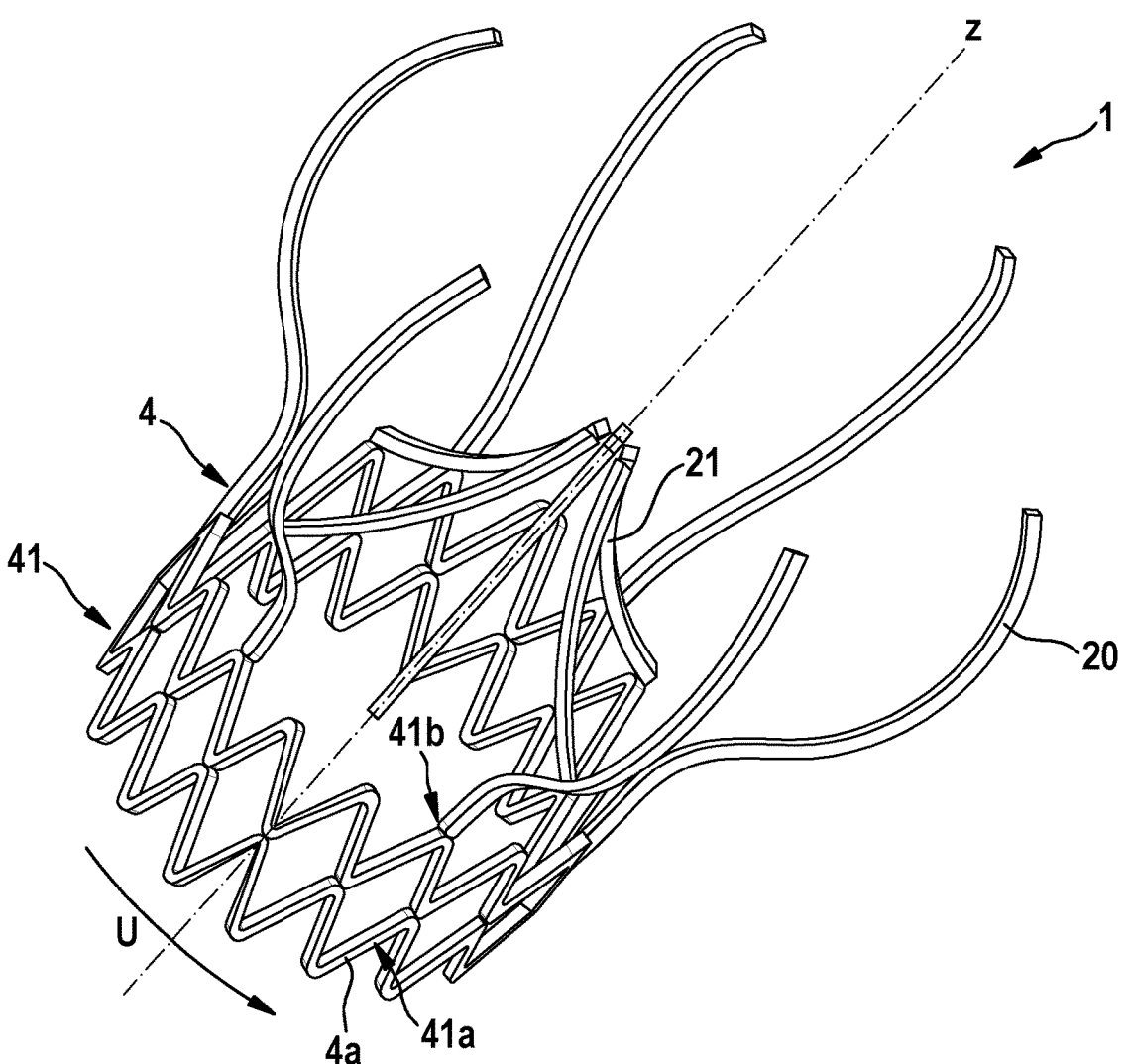

Furthermore, according to an aspect of the invention shown in FIG. 14, it is provided that the support structure 4 has only a single annular structure 41 of cells 41*a* which are interconnected in the circumferential direction U of the support structure 4, in particular diamond-shaped cells 41*a* which are formed from interconnected struts 4*a*, wherein for anchoring the prosthetic venous valve 1 in the vein, atrau- matically rounded stirrups 20 project from the annular structure 41 and are extended along the axis z of the support structure 4, wherein these stirrups 20 have free ends which in particular do not adjoin a further annular structure.

Optionally, the support structure 4 according to FIG. 14 may also have stirrups 21 that extend inwardly from the single ring structure 41 into the vein lumen to prevent possible puncture of the valve leaflets 5*a*, 5*b* (not shown) at high hydrostatic pressure. The valve arrangement 5*a*, 5*b* or the valve leaflets 5*a*, 5*b* are preferably connected to the support structure 4 via the single ring structure 41.

While specific embodiments of the present invention have been shown and described, it should be understood that other modifications, substitutions and alternatives are apparent to one of ordinary skill in the art. Such modifications, substi- tutions and alternatives can be made without departing from the spirit and scope of the invention, which should be determined from the appended claims.

Various features of the invention are set forth in the appended claims

The invention claimed is:

1. A venous valve prosthesis for transporting blood in a vein in a predetermined direction, comprising:
   a hollow-cylindrical support structure;
   a skirt connected to the support structure forming a closed, circumferential jacket of the support structure; and
   a valve leaflet arrangement with a first valve leaflet and a second valve leaflet, each being connected to the skirt, wherein a downstream edge of the first valve leaflet and a downstream edge of the second valve leaflet are opposite to each other and configured in such a manner that in a first state of the valve leaflet arrangement they form an opening for blood to flow through in the predetermined direction and in a second state of the valve leaflet arrangement the opening is closed to prevent a backflow of blood in a direction opposite to the predetermined direction, wherein the ratio of the inner diameter of the support structure to its length in the predetermined direction is at most 1, wherein the support structure comprises interconnected struts con- figured such that, in the implanted state, they rest against an inner vessel side of the vein over most of their length, wherein the two valve leaflets are each connected with an upstream edge to the skirt, and wherein a first end of the downstream edge of each of the first valve leaflet and the second valve leaflet are connected to each other and to an apex of a first arcuate strut of the support structure, wherein a second end of the downstream edge of each of the first valve leaflet and the second valve leaflet are connected to each other and to an apex of a second arcuate strut of the support structure, wherein the first arcuate strut and the second arcuate strut oppose each other in a direction transverse to the predetermined direction and are movable in a direction transverse to the predetermined direction such that a transition from the first state to the second state of the valve leaflet assembly can be effected upon an increase in the inner diameter of the vein.

2. The venous valve prosthesis according to claim 1, wherein the first arcuate strut and the second arcuate strut are not connected to a downstream adjacent strut row.

3. The venous valve prosthesis according to claim 2, wherein the downstream adjacent strut row in the region of the apex of the first arcuate strut and in the region of the apex of the second arcuate strut runs parallel to the first arcuate strut and to the second arcuate strut, respectively, preferably at a distance between 0.5 mm and 15 mm.

4. The venous valve prosthesis according to claim 1, wherein the entire non-downstream and exposed edge of the first valve leaflet and the second valve leaflet are each connected to the arcuate strut.

5. The venous valve prosthesis according to claim 1, wherein the first arcuate strut and the second arcuate strut are interconnected via a substantially elliptical structure of the support structure.

6. The venous valve prosthesis according to claim 5, wherein the elliptical structure forms the upstream edge of the skirt.

7. The venous valve prosthesis according to claim 1, wherein the support structure extends along an axis coin- ciding with the predetermined direction, the support struc- ture further comprising a first annular structure surrounding an inflow region of the venous valve prosthesis and a second annular structure spaced therefrom and surrounding an out- flow region of the prosthetic venous valve, wherein the second annular structure faces the first annular structure, and wherein the two annular structures are interconnected by longitudinal connectors extending along the axis.

8. The venous valve prosthesis according to claim 7, wherein the first annular structure comprises a plurality of cells interconnected in the circumferential direction, each cell of the first annular structure being formed by struts interconnected with each other, and/or the second annular structure comprises a plurality of cells interconnected in the circumferential direction, each cell of the second annular structure being formed by struts interconnected with each other.

9. The venous valve prosthesis according to claim 8, wherein the support structure is structured to be transferable from a compressed state, in which the venous valve pros- thesis is implantable in the vein, to an expanded state, in which the support structure is anchorable in the vein.

10. The venous valve prosthesis according to claim 9, wherein the cells are diamond-shaped in the expanded state of the support structure.

11. The venous valve prosthesis according to claim 7, wherein the two ring structures are configured for anchoring the venous valve prosthesis in the vein.

12. The venous valve prosthesis according to claim 7, wherein the first and the second annular structures are interconnected by a first and a second longitudinal connec- tor, each longitudinal connector is arcuate with respect to an unwound state of the support structure in which the support structure extends two-dimensionally in a plane, and has an apex region and two ends.

13. The venous valve prosthesis according to claim 12, wherein the apex region of the respective longitudinal connector is connected to the first annular structure, and the two ends of the respective longitudinal connector are con- nected to the second annular structure.

14. The venous valve prosthesis according to claim 13, wherein the apex region of the respective longitudinal connector adjoins a tip of a cell of the first annular structure.

15. The venous valve prosthesis according to claim 12, wherein the valve leaflet assembly is connected to the support structure via the longitudinal connectors.

16. The venous valve prosthesis according to claim 7, wherein the two ring structures are connected to each other by longitudinal connectors extending along the axis, which connectors are each arched outwardly in the radial direction of the supporting structure with respect to the expanded state of the supporting structure and are configured to press against an inner vessel wall of the vein for anchoring the venous valve prosthesis.

17. The venous valve prosthesis of claim 16, wherein the valve leaflet assembly is fixed to the two annular structures.

18. The venous valve prosthesis according to claim 17, wherein the skirt is fixed to the first annular structure, the skirt being arranged on an outer side and/or on an inner side of the first annular structure.

19. The venous valve prosthesis according to claim 1, wherein the skirt and/or the valve leaflets is/are formed of at least one of the following materials or comprises at least one of the following materials, wherein the respective material is preferably electrospun: a polyurethane (PU), a polycarbonate urethane (PCU) or a copolymer (TSPCU), such as polycarbonate urethane-co-silicone (PCU-co-Si B), a polyurethane-co-silicone (PU-co-Si A), a thermoplastic copolyester elastomer (TPC-ET), expanded polytetrafluoroethylene (ePTFE), polyvinylidene fluoride (PVDF), poly(vinylidene fluoride-co-hexafluoropropylene) (PVDF-co-HFP), polyacrylonitrile (PAN), and dual- or co-axial electrospun composites or fiber composites of the above materials including polyvinylpyrrolidone and hyaluronic acid (PVP/HA).

\* \* \* \* \*